US007971389B2

(12) United States Patent
Patane et al.

(10) Patent No.: US 7,971,389 B2
(45) Date of Patent: Jul. 5, 2011

(54) ENHANCING ENZYME PRODUCTION

(75) Inventors: Michael Patane, Seaforth (AU); Mitchell Parker, Seaforth (AU); Akshat Talwalkar, Seaforth (AU); Bernard Parker, Silverwater (AU)

(73) Assignees: Protech Research Pty Ltd., Seaforth (AU); Emu AG, Kussnacht An Rigi (CH)

( * ) Notice: Subject to any disclaimer, the term of this patent is extended or adjusted under 35 U.S.C. 154(b) by 258 days.

(21) Appl. No.: 11/991,022

(22) PCT Filed: Aug. 25, 2006

(86) PCT No.: PCT/AU2006/001242
§ 371 (c)(1),
(2), (4) Date: Apr. 20, 2009

(87) PCT Pub. No.: WO2007/022598
PCT Pub. Date: Mar. 1, 2007

(65) Prior Publication Data
US 2009/0217579 A1 Sep. 3, 2009

(30) Foreign Application Priority Data
Aug. 26, 2005 (AU) ................................ 2005904664

(51) Int. Cl.
C12N 5/04 (2006.01)
A01C 1/06 (2006.01)
A01H 4/00 (2006.01)
(52) U.S. Cl. ........................... 47/58.1; 47/57.6; 435/420
(58) Field of Classification Search ........................ None
See application file for complete search history.

(56) References Cited

U.S. PATENT DOCUMENTS
3,134,724 A  5/1964 Beckord et al.
3,754,929 A * 8/1973 Palmer ............................ 426/28
5,045,328 A  9/1991 Lewis et al.

FOREIGN PATENT DOCUMENTS
WO   WO 85/04556     10/1985
WO   WO 01/47364      7/2001
WO   WO 2007/022598   3/2007

OTHER PUBLICATIONS

Dahlstrom et al. Relationship of Gibberellic Acid to Enzyme Development. InGIBBERELLINS; Advanced in Chemistry: American Chemical Society: Washington, DC, 1961.*
Diedering,P. (1943) Colloidal behaviour and enzymic degradation of starch and a contribution on decreasing sprout injury, Z.ges. Getreidew 30:1-17 (Whole document).
Hirasawa, E., et al, (1994) Effects of wounding, ethylene and abscisic acid on the development of α-amylase activity in detached cotyledons of Pisum sativuml, Journal of Plant Physiology, 143:359-362 (Whole document).
Ichinose, Y., et al, (2001) Effects of increase in α-amylase and endoprotease activities during germination on the breadmaking quality of wheat, Food Science Technology Research 7(3):214-219 (Abstract; p. 215).
Moot, D.J., & Every, D. (1990) A comparison for bread baking, falling number, α-amylase assay and visual method for the assessment of pre-harvest sprouting in wheat, Journal of Cereal Science 11:225-234 (Abstract, p. 231).
Schlimme, G. (1977) Abrasion of winter barley (Schleifen von Wintergerste) Brauwelt 117(49):1894-1895 (Whole document, p. 1895).
International Search Report issued Oct. 19, 2006 for International Patent Application No. PCT/AU2006/01242, which was filed on Aug. 25, 2006 and published as WO 2007/022598 on Mar. 1, 2007 (Inventors: Patane et al.; Applicant: Protech Research Pty. Ltd.).
International Preliminary Report on Patentability with Written Opinion issued Feb. 26, 2008 for International Patent Application No. PCT/AU2006/01242, which was filed on Aug. 25, 2006 and published as WO 2007/022598 on Mar. 1, 2007 (Inventors: Patane et al.; Applicant: Protech Research Pty. Ltd.).
Response filed Oct. 16, 2009 for Singapore Application No. 200801565-3, which is a national phase application of PCT/AU2006/01242, which was filed on Aug. 25, 2006 (Inventors: Patane et al.; Applicant: Protech Research Pty. Ltd.).
Invitation to Respond to Written Opinion issued May 18, 2009 for Singapore Application No. 200801565-3, which is a national phase application of PCT/AU2006/01242, which was filed on Aug. 25, 2006 (Inventors: Patane et al.; Applicant: Protech Research Pty. Ltd.).
Examination Report issued Jan. 21, 2010 for Singapore Application No. 200801565-3, which is a national phase application of PCT/AU2006/01242, which was filed on Aug. 25, 2006 (Inventors: Patane et al.; Applicant: Protech Research Pty. Ltd.).
Noting of loss of rights pursuant to Rule 112(1) EPC issued Nov. 2, 2009 for European Patent Application No. 06774871.5-2406, which is a national phase application of PCT/AU2006/01242, which was filed on Aug. 25, 2006 (Inventors: Patane et al.; Applicant: Protech Research Pty. Ltd.).
Communication pursuant to Article 94(3) EPC issued May 18, 2009 for European Patent Application No. 06774871.5-2406, which is a national phase application of PCT/AU2006/01242, which was filed on Aug. 25, 2006 (Inventors: Patane et al.; Applicant: Protech Research Pty. Ltd.).
Response filed Dec. 23, 2009 for European Patent Application No. 06774871.5-2406, which is a national phase application of PCT/AU2006/01242, which was filed on Aug. 25, 2006 (Inventors: Patane et al.; Applicant: Protech Research Pty. Ltd.).
Examination Report issued Mar. 3, 2010 for New Zealand Patent Application No. 566918, which is a national phase application of PCT/AU2006/01242, which was filed on Aug. 25, 2006 (Inventors: Patane et al.; Applicant: Protech Research Pty. Ltd.).

(Continued)

Primary Examiner — Annette Para
(74) Attorney, Agent, or Firm — Ballard Spahr LLP

(57) ABSTRACT

The invention relates to a process for increasing the amount of enzymes in a grain by germinating the grain in conditions in which the grain is wounded. The invention also relates to hydrolases obtainable from grains for use in food processing and manufacturing industries, to the germination of grains such as barley and to isolation of enzymes from grains.

19 Claims, No Drawings

OTHER PUBLICATIONS

Response to Examination Report filed Sep. 7, 2010 for New Zealand Patent Application No. 566918, which is a national phase application of PCT/AU2006/01242, which was filed on Aug. 25, 2006 (Inventors: Patane et al.; Applicant: Protech Research Pty. Ltd.).

Examination Report issued Sep. 21, 2010 for New Zealand Patent Application No. 566918, which is a national phase application of PCT/AU2006/01242, which was filed on Aug. 25, 2006 (Inventors: Patane et al.; Applicant: Protech Research Pty. Ltd.).

Response to Examination Report filed Dec. 15, 2010 for New Zealand Patent Application No. 566918, which is a national phase application of PCT/AU2006/01242, which was filed on Aug. 25, 2006 (Inventors: Patane et al.; Applicant: Protech Research Pty. Ltd.).

Notification of the First Office Action issued Apr. 23, 2010 for Chinese Patent Application No. 200680035320.4, which is a national phase application of PCT/AU2006/01242, which was filed on Aug. 25, 2006 (Inventors: Patane et al.; Applicant: Protech Research Pty. Ltd.).

Claim Amendments after First Office Action for Chinese Patent Application No. 200680035320.4, which is a national phase application of PCT/AU2006/01242, which was filed on Aug. 25, 2006 (Inventors: Patane et al.; Applicant: Protech Research Pty. Ltd.).

* cited by examiner

ENHANCING ENZYME PRODUCTION

CROSS REFERENCE TO RELATED APPLICATIONS

The present application is a National Phase Application of International Application No. PCT/AU2006/001242, filed Aug. 25, 2006, which claims priority to Australian Patent Application No. 2005904664 filed Aug. 26, 2005, which applications are incorporated herein fully by this reference.

FIELD OF THE INVENTION

The invention relates to hydrolases obtainable from grains for use in food processing and manufacturing industries, to the germination of grains such as barley and to isolation of enzymes from grains.

BACKGROUND OF THE INVENTION

Many hydrolytic enzymes of grains, of which limit dextrinase (EC 3.2.1.142), α and β amylase (EC 3.2.1.1 and EC 3.2.1.2 respectively), 1-6-β-glucanase (EC 3.2.1.39), β1,4-xylanase (EC-3.2.1.8), arabinoxylanase (EC 3.2.1.136), and β glucosidase (EC 3.2.1.21) are examples, have found application in a variety of industries, and in particular, in food processing and manufacturing industries.

These enzymes, otherwise known as hydrolases, are typically obtained for commercial application from tissues such as plant tissue, including grains, pulses, legumes and the like and bacterial fermentations and the like. In some circumstances these enzymes may be produced in recombinant expression systems.

A problem with some of the processes by which many hydrolases are obtained for commercial application is that they tend to provide for a sub-optimal yield of hydrolase. Hence, considerable expense is incurred in obtaining commercial quantities of hydrolases.

There is a need for improvements in processes for obtaining hydrolases, especially improvements that are associated with improved yields of hydrolases.

SUMMARY OF THE INVENTION

In summary, in certain embodiments there is provided a process for increasing the amount of, or expression of an enzyme in a grain.

In other embodiments there is provided a process for producing a grain having a high relative abundance of an enzyme.

In other embodiments there is provided a process for producing an enzyme.

In further embodiment there is provided a process for extracting, purifying or isolating an enzyme for a grain having a high relative abundance of an enzyme.

Typically the process involves wounding a grain that is undergoing germination to form a wounded grain having at least one site of tissue damage that can be at least partially repaired by the wounded grain and permitting the wounded grain to at least partially repair an at least one site of tissue damage of the wounded grain to form a repaired grain. Otherwise stated, conditions are provided to a grain that provide for germination of a grain and that provide for one or more wounds to be applied to a grain. These conditions provide for a wound applied to a grain to be repaired by the grain.

In some embodiments the process includes allowing a rootlet to grow from a grain, removing the rootlet from the grain and growing a further rootlet from the grain.

In certain embodiments, a process for extracting, purifying or isolating an enzyme from a grain having a high relative abundance of an enzyme includes the further step of releasing or otherwise extracting and/or purifying or isolating an enzyme from a grain having a high relative abundance of an enzyme.

In further embodiments there is provided a grain having a high relative abundance of an enzyme. The grain is typically formed from a process involving providing conditions to a grain that provide for germination of the grain and for one or more wounds to be applied to the grain. These conditions also provide for a wound on a grain to be repaired by the grain.

DETAILED DESCRIPTION OF THE EMBODIMENTS

It has been found that the expression of hydrolases can be significantly increased, leading to a significant increase in the relative abundance or otherwise relative amount of a hydrolase in a tissue, in circumstances wherein a tissue is wounded and permitted to repair. Specifically, as described herein, it has been found that barley grains grown in conditions in which the grains were subjected to wounding and repair had amounts of hydrolases, α-amylase EC 3.2.1.1 and β-amylase EC 3.2.1.2, as much as 1.7 fold and 0.05 fold greater than barley grains grown in conditions not involving wounding and repair. Other hydrolases, limit dextrinase EC 3.2.1.142 and β1,4-xylanase EC 3.2.1.8 were found in up to 16.8 and 6.5 fold greater amounts in these grains.

These findings are particularly significant because when the grains the subject of injury and repair are processed for release of enzymes according to commercial extraction processes or otherwise, improved yields of hydrolytic enzymes can be obtained.

Thus in certain embodiments there is provided a process for increasing the amount of, or expression of an enzyme in a grain. The process includes the step of providing conditions to a grain that provide for germination of the grain and for one or more wounds to be applied to the grain, or in other words, for germinating a grain in conditions in which the grain is wounded by application of one or more wounds to the grain.

In other embodiments there is provided a process for producing a grain having a high relative abundance of an enzyme. The process includes the step of providing conditions to a grain that provide for germination of the grain and for one or more wounds to be applied to the grain.

In one embodiment, the grain is a barley grain. However, it will be understood that other grains may be processed, including, for example, rice, wheat, corm, maize and the like. Further, legumes and pulses such as lentils, soybeans and the like may also be processed.

It is important that the greater proportion of grains subjected to the process are not lethally wounded. A lethal wound tends to be one that results in death of a grain embryo, or one that otherwise prevents a grain from at least partially repairing a wound applied to the grain,—or otherwise from germinating.

Further, as discussed in more detail below, it has been found that a live grain embryo is associated with the enhanced secretion of one or more enzymes from a grain during germination.

The grain may be wounded by applying a physical treatment to the grain. Physical treatments include those that result in abrasion, laceration, tumbling, agitation or compression of the grain. Other forms of physical treatment are contemplated.

Particularly useful physical treatments are those that cause injury to a rootlet or part thereof such as a rootlet tip, or that remove a rootlet or part thereof from a grain, or an injury to a shoot, grain husk or pericarp. A treatment that results in an affect on an outer layer of a grain, aleurone layer or hemicellulose layer or like may also be useful.

An example of a process for abrasion of a grain is shown in U.S. Pat. No. 3,754,929. A process for compression of a grain is shown in U.S. Pat. No. 4,052,795.

Grain may also be wounded by one or more of chemical treatment, exposure to temperature, pressure or radiation.

Chemical treatments include alkali treatment. This treatment is particularly useful, among other things, for solubilizing or partially solubilizing the grain husk. An example of an alkali treatment is one wherein grains are conditioned over a time course of 24 hours during a second steep.

Other forms of chemical treatment include treatment with ammonia. An example of chemical treatment with ammonia is shown in U.S. Pat. No. 3,134,724.

As noted above, the grain may be wounded by heating the grain. Generally speaking, a grain should not be heated beyond 40° C. as above these temperatures, a grain embryo may be lethally wounded. Heating is generally performed during a second steep. Heating may be useful for softening a glucan outer husk of a grain.

A particularly useful wounding regimen is to apply a treatment to the grain that causes removal of a rootlet from the grain and in which repair mechanisms cause re-growth of a further rootlet from the wounded grain. In certain embodiments the rootlets are grown to about 5 to 7 days from the start of germination, although other time periods may be appropriate. Generally it is preferred to have removed rootlets before 12 days from the start of germination, and in some instances, earlier than this, for example, 10 days from the start of germination.

Although it is particularly useful to remove roots, rootlets, rot tips and shoots and shoot tips, in certain embodiments other grain organs may be removed, examples of which include grain husk and associated layers.

Generally speaking, roots, shoots or the like need only be removed once from a grain for there to be an enhancement in enzyme production beyond that observed in unwounded grain. In certain embodiments, a treatment for wounding a grain is applied repeatedly. This has advantages for ensuring that all grains are wounded at least once, for example by removal of a root, shoot or the like once from each grain. This may be useful particularly as at any one time that a treatment is applied, not all grains may have reached the same stage of development of organ. Further in certain embodiments it is advantageous to remove more than one root, shoot or the like from a grain.

It will be understood that it is not necessary to re-injure a repaired grain. Further, it is not necessary that an injured grain undergo complete repair.

An example of an apparatus for applying a wound is shown in U.S. Pat. No. 3,174,909. Generally, an apparatus may be comprised of a drum for holding grains, the drum having an internal baffle, in use, for agitating grains contained in the drum when the drum is rolled, and a roller for rolling the drum.

Thus in certain embodiments there is provided a process for increasing the amount of a hydrolytic enzyme in a grain including:
  allowing a rootlet to grow from a grain;
  removing the rootlet from the grain; and
  allowing a further rootlet to grow from the grain, to increase the amount of a hydrolytic enzyme in a grain.

Germination is generally recognised as a process characterised by one or more of hydration of tissue leading to modulation of volume of a grain, modulation of enzyme activity, change in endosperm structure and composition and modulation of embryo activity.

Typically, the grains to which conditions for injury and repair are applied are grains that are undergoing germination i.e. grains that at the time of application of injury are about to germinate, or grains that are in an active state of germination at the time of application of injury, or grains that have completed germination at the time of application of injury.

In certain embodiments, the grains are in an active state of germination at the time of application of injury and remain in that state during repair and subsequent further injury and repair steps.

Typically, the grains have a moisture content of about 40% or less at the time that the injury and repair processes occur. The moisture content is a proportion of dry weight over hydrated weight. A moisture content of about 30-35% as a proportion of dry weight is particularly useful in certain embodiments.

Generally the moisture content is more than about 10%, more than about 15%, about 20%, about 25%, about 30% to 35% and generally should not exceed 40%.

In certain embodiments, the moisture content is more than about 25% after steeping and about 30% to 35% post an extended germination period and should not exceed 40% at any time. The desired moisture content may be obtained by steeping the grains in an appropriate aqueous solution. The solution may simply be water, or it may include other compounds such as growth promoters, such as gibberellic acid, anti-microbials (such as $SO_2$) especially anti-fungals, or other compounds such as $NH_4OH$ alkalis to soften the grain and raise the pH.

The steep may consist of a single steeping step, or it may consist of multiple steeping steps, each step characterised according to the conditions applied during each steep. For example a first steep might include conditions in which grain is hydrated to less than about 40%. For example a grain may be hydrated from an initial grain moisture of about 10% to about 20% moisture content in the presence of about 50 ppm $SO_2$ for about 12-24 hours in the first steep. This solution may then be removed to exclude any bacteria and avoid any continued reaction with $SO_2$ on surface proteins or glucans. A second steep step might include adjusting hydration of the grain to about 20-30% moisture content at an increased pH up to 8.0, in the presence of 5-20 ppm gibberellic acid and perhaps some minor heating to 40° C. in the last hour for a total steeping time of 12-24 hours.

In certain embodiments, the grain is steeped for about 5 days, although it may be steeped for fewer days, for example, 1, 2, 3 or 4 days. Further, there may be benefit in steeping the grain for longer than 5 days. However, in these circumstances it becomes more difficult to control fungal contamination during the steeping process.

Further, a grain may be subjected to injury and/or repair prior to steeping, during steeping, or after steeping (i.e. at "steep out").

It will be understood that in certain embodiments conventional steeping steps may not be required.

Where one or more steeping steps are implemented, the grain may be injured and permitted to repair for a period of up to 12 days after the completion of the steeping steps, although injury and repair may occur across a greater time. The length of time is dependent in part on the enzymes that are increased in the grain. Times that are suitable to specific grains are discussed further herein. In certain embodiments, the grain is injured and permitted to repair about 3 days after steeping is completed, about 5 days after steeping is completed or about 10 days after steeping is completed. During these times, the grain may be treated with a growth promoter such as gibberellic acid and maintained at less than 35% moisture in the presence of light.

In certain embodiments the conditions are controlled so as to minimise respiration of the grains during steeping or germination. Respiration is generally understood as a process by which energy is released from molecules such as carbohydrates. One advantage of limiting respiration is to minimise the extent of biochemical processes that are unrelated to wound repair, and hence conserve and direct available energy to wound repair, hence leading to increases in synthesis of a hydrolytic enzyme in a grain. Another advantage is to limit the production of molecules associated with respiration, such as sugars and $CO_2$ and the like which would support growth of contaminating microbes such as fungi and the like.

One way of minimising respiration is to control the moisture content of the grains undergoing germination and/or steeping. This can be achieved by controlling the relative humidity of the environment during germination and/or steeping, i.e. by controlling the temperature and moisture content of the environment. Generally it is preferable to provide conditions for minimising respiration which prevent starch granules in the grain from bursting. In one embodiment the relative humidity is about 80% and the temperature is less than about 20° C., preferably about 10 to 15° C.

In certain embodiments, the grain may be treated to eliminate microbes located on the surface of the grain. This may be useful for at least limiting contamination of the grain as the grain is undergoing germination. Particularly useful treatments are those that kill fungi, or fungal spores that would otherwise enable fungi to grow on grain during grain germination. Examples include washing in an anti-microbial, gassing in $SO_2$ or ammonia, treatment with urea, irradiation, especially UV irradiation, exposure to light.

An additional or alternative approach is to prevent root or shoot development from penetrating through the grain husk. In some circumstances, penetration of the husk by these organs provides opportunity for micro-organisms to infect the endosperm.

It will be understood that further enhancements in relative abundance of particular hydrolases in a grain can be obtained by modifying steeping conditions. Examples of modifications that are relevant to particular hydrolases are discussed further herein.

One particular advantage of the process discussed herein is that the grains obtained therefrom can be subjected to further downstream processing, such as for example to purify or otherwise extract enzymes from these grains. For example, the grains obtained from the process discussed herein could be subjected to the process discussed in U.S. Pat. No. 4,355,110 to purify pullulenase.

The process discussed herein is particularly useful for enhancing the expression of grain hydrolases, especially those located in the aleurone and starch endosperm layers, and embryo. Examples of enzymes include limit dextrinase, α and β amylase, 1-6-β-glucanase, β1,4-xylanase, arabinoxylanase, lipoxygenase and β glucosidase α and β amylase may be obtained in enhanced amounts by a 2 day steep and 3 days germination.

Limit dextrinase may be obtained in enhanced amounts by a 2 day steep and 7-8 days germination.

Xylanase may be obtained in enhanced amounts by a 2 day steep and 10-12 days germination.

EXAMPLE

Grains were steeped as described for 2 days and were then incubated for a further 10 to 15 days in conditions including:
UV illumination to retard microbial growth;
controlled temperature between about 7 and 13° C., normally about 10° C.;
controlled relative humidity at 80% with passive recirculating air flow;
periodic tumbling for 30 minute periods to prevent rootlets and shoots from penetrating the grain husk, each tumbling period followed by a 3 hour rest period.

The invention claimed is:

1. A process for increasing the amount of one or more grain hydrolases in a grain including germinating a grain in conditions in which one or more selected organs or tissues of the grain is non-lethally wounded, wherein the one or more organs or tissues is selected from the group consisting of a rootlet, a root tip, a shoot, and a shoot tip, and wherein the conditions provide for repair, growth, or regrowth of the rootlet, root tip, shoot, or shoot tip.

2. A process according to claim 1 wherein the grain is germinated in conditions in which a physical treatment is applied to the grain to wound the grain.

3. A process according to claim 2 wherein the physical treatment is applied to the grain by tumbling, agitating or compressing the grain.

4. A process according to claim 1 wherein the grain is germinated in conditions in which a chemical or heat treatment is applied to the grain to wound the grain.

5. A process according to claim 1 wherein the selected organ or tissue is a rootlet or root tip of the grain.

6. A process according to claim 1 wherein the grain is germinated in conditions in which a physical treatment is applied to the grain to partially or completely remove a rootlet from the grain.

7. A process according to claim 6 wherein the conditions provide for growth or for regrowth of a rootlet from the grain.

8. A process according to claim 1 wherein the grain has a moisture content of about 40% or less.

9. A process according to claim 1 including a step of steeping the grain in an aqueous solution prior to germinating the grain.

10. A process according to claim 9 wherein the grain is steeped to provide the grain with a moisture content of about 40% or less.

11. A process according to claim 9 wherein the aqueous solution includes one or more compounds selected from the group consisting of a growth promoter, an anti-microbial or an alkali.

12. A process according to claim 11 wherein the grain is steeped in more than one aqueous solution.

13. A process according to claim 12 wherein the grain is initially steeped in an aqueous solution including 50 ppm $SO_2$ to increase the moisture content of the grain to about 20%.

14. A process according to claim 13 wherein the grain is further steeped in an aqueous solution including 5 to 20 ppm gibberellic acid and having a pH of about 8.0 to increase the moisture content of the grain to about 40%.

15. A process according to claim 9 wherein the grain is steeped for about 5 days or less.

16. A process according to claim 1 wherein the grain is germinated in conditions in which the grain is wounded for up to 12 days.

17. A process according to claim 1 wherein the selected organ or tissue is a shoot or shoot tip.

18. A process according to claim 1 wherein the selected organ or tissue is a rootlet or a root tip and a shoot or shoot tip.

19. A process according to claim 1 wherein the one or more grain hydrolases is selected from the group consisting of α-amylase, β-amylase, limit dextrinase and xylanase.

* * * * *